(12) United States Patent
Barrett et al.

(10) Patent No.: US 8,926,532 B2
(45) Date of Patent: Jan. 6, 2015

(54) GONIOMETER

(75) Inventors: Philip Barrett, Leeds (GB); Alec Birkbeck, Leeds (GB); James Brooks, Leeds (GB); Andrew Burton, Leeds (GB); Marcellino Maheson, Leeds (GB)

(73) Assignee: Depuy International Limited, Leeds (GB)

( * ) Notice: Subject to any disclaimer, the term of this patent is extended or adjusted under 35 U.S.C. 154(b) by 623 days.

(21) Appl. No.: 13/063,425

(22) PCT Filed: Sep. 11, 2009

(86) PCT No.: PCT/GB2009/051175
§ 371 (c)(1),
(2), (4) Date: Jul. 27, 2011

(87) PCT Pub. No.: WO2010/029368
PCT Pub. Date: Mar. 18, 2010

(65) Prior Publication Data
US 2011/0275958 A1    Nov. 10, 2011

(30) Foreign Application Priority Data

Sep. 12, 2008  (GB) .................... 0816638.1

(51) Int. Cl.
*A61B 5/103* (2006.01)
*A61B 17/17* (2006.01)
*A61B 5/107* (2006.01)
*A61F 2/46* (2006.01)
*A61B 5/00* (2006.01)
*A61B 19/00* (2006.01)

(52) U.S. Cl.
CPC ........... *A61B 17/1721* (2013.01); *A61B 5/1071* (2013.01); *A61B 17/175* (2013.01); *A61F 2/4607* (2013.01); *A61F 2/4657* (2013.01); *A61B 5/103* (2013.01); *A61B 5/4528* (2013.01); *A61B 19/26* (2013.01); *A61B 2019/467* (2013.01); *A61F 2002/4668* (2013.01); *A61F 2002/4687* (2013.01); *A61F 2002/4628* (2013.01)
USPC ................ 600/595; 600/587; 33/511; 33/512

(58) Field of Classification Search
CPC ..... A61B 5/4528; A61B 5/103; A61B 5/0053
USPC ............................ 33/511, 512; 600/587, 595
See application file for complete search history.

(56) References Cited

U.S. PATENT DOCUMENTS

| 3,229,372 A | 1/1966 | Quashnock |
| 4,930,525 A | 6/1990 | Palestrant |

(Continued)

FOREIGN PATENT DOCUMENTS

WO    WO 9806359 A1    2/1998

OTHER PUBLICATIONS

PCT International Search Report and Written Opinion PCT/GB2009/051072, dated Dec. 3, 2009.

(Continued)

*Primary Examiner* — Sean Dougherty
*Assistant Examiner* — Daniel Cerioni (57) ABSTRACT

A goniometer comprises a first arm (2), a second arm (4) and a connecting portion (6) pivotally connecting the first arm (2) to the second arm (4) about a pivot axis (7). An instrument connector (8) is coupled to the first arm (2) arranged to couple to a surgical instrument (10). A method of aligning a surgical instrument (10) using the goniometer is also disclosed.

13 Claims, 8 Drawing Sheets

(56) References Cited

U.S. PATENT DOCUMENTS

| | | | |
|---|---|---|---|
| 5,188,121 A * | 2/1993 | Hanson | 600/594 |
| 5,196,019 A | 3/1993 | Davis | |
| 5,263,492 A * | 11/1993 | Voyce | 600/595 |
| 5,792,077 A * | 8/1998 | Gomes | 600/595 |
| 6,273,915 B1 * | 8/2001 | Grimes | 623/23.21 |
| 6,361,506 B1 * | 3/2002 | Saenger et al. | 600/587 |
| 6,796,986 B2 | 9/2004 | Duffner | |
| 6,872,187 B1 * | 3/2005 | Stark et al. | 602/16 |
| 7,018,383 B2 | 3/2006 | McGuire | |
| 7,571,548 B2 | 8/2009 | Taylor et al. | |
| 7,837,635 B2 * | 11/2010 | Lissek et al. | 600/595 |
| 2002/0165552 A1 | 11/2002 | Duffner | |
| 2007/0266579 A1 | 11/2007 | Briscoe | |

OTHER PUBLICATIONS

UK Search Report GB0816638.1, dated Dec. 6, 2008.
Chinese Search Report CN200980136095.7 dated Sep. 17, 2013.
Australian Search Report for Corresponding Australian Patent Application No. 2009290650 Dated Jan. 9, 2014, 3 Pages.
Japanese Search Report for Corresponding Japanese Patent Application No. 2011-526573 Dated Sep. 19, 2013, 7 Pages.

\* cited by examiner

GONIOMETER

CROSS REFERENCE TO RELATED APPLICATION

This application is a National Stage 35 U.S.C. 371 of International Patent Application PCT/GB2009/051175 filed Sep. 11, 2009.

The present invention relates to a goniometer. In particular, the present invention relates to a goniometer for use during a surgical procedure to align a surgical instrument. The invention further relates to a method of using the goniometer to align a surgical instrument.

BACKGROUND OF THE INVENTION

A goniometer is an instrument for measuring angles. Goniometers are known for use in medicine for measuring the relative angles of various anatomical points.

U.S. Pat. No. 229,372 discloses a goniometer for measuring angular movement of joints between bones in a human body. The goniometer comprises a protractor head having an arcuate sector with an angle indicating scale. The ends of the arcuate sector are joined to an elongated base section arranged to be aligned with a body part, for instance the upper leg, with the centre of the arcuate section aligned with a joint, for instance the knee. A pointing arm is rotatably coupled to the base section at the centre of the arcuate section and is arranged to be aligned with a second body part, for instance the lower leg. The position of the pointing arm relative to the arcuate section is indicative of the angle of the joint.

US-2007/0266579-A1 discloses a similar goniometer for performing range of motion measurements upon a human patient.

During orthopedic surgery it is a common requirement to be able to align surgical instruments, such as a drill guide, or a prosthesis with a body axis, or at a predetermined angle relative to the body axis. Commonly, the correct alignment of the instrument or the prosthesis is dependent upon visual inspection and the skill of the surgeon.

It is an object of embodiments of the present invention to obviate or mitigate one or more of the problems of the prior art, whether identified herein or elsewhere.

BRIEF SUMMARY OF THE INVENTION

According to a first aspect of the present invention there is provided a goniometer comprising: a first arm; a second arm; a connecting portion pivotally connecting the first arm to the second arm about a pivot axis; and an instrument connector coupled to the first arm arranged to couple to a surgical instrument.

An advantage of goniometers in accordance with the first aspect of the invention is that surgical instruments, such as drill guides, may be directly referenced to a body axis at a predetermined angular offset. For instance, a drill guide may be accurately positioned relative to an anatomical intersection aligned with the pivot axis of the goniometer and a body axis of the patient aligned with the second arm of the goniometer.

The instrument connector may comprise a sleeve arranged to pass over and slide along a surgical instrument, such that the surgical instrument can engage a bone. In particular, the sleeve may be arranged to pass over a drill guide, such that aligning the second arm of the goniometer with a body axis and positioning the pivot axis over an anatomical feature correctly locates the drill guide at a required angle for forming a bore extending into a bone. During positioning of the goniometer the drill guide may be allowed to slide within the sleeve and pivot about a first end in contact with a surface of a bone.

The axis of the bore of the sleeve may be arranged to be parallel to the axis of the first arm proximal to the connecting portion and to intersect the pivot axis of the connecting portion. Alternatively, the bore of the sleeve may be arranged to be at a predetermined angle relative to the axis of the first arm proximal to the connecting portion. Preferably the axis of the sleeve is offset from the axis of the proximal part of the first arm along the pivot axis.

The second arm may be extendable. Alternatively, the second arm may be of fixed length. The second arm is arranged to be aligned with a body axis to position the goniometer.

The first arm may comprise a first part extending from the connecting portion and a second part extending transversely from the first part such that the instrument connector is spaced apart from the axis of the first part of the first arm. The second part of the first arm may be coupled to the first part of the first arm such that the distance between the instrument connector and the axis of the first arm is adjustable. Advantageously, this allows the goniometer to be adjusted to accommodate different weight patients. Preferably, the coupling between the first part and the second part is arranged to ensure that the sleeve axis cannot rotate relative to the axis of the proximal part of the first arm (that is, such that the sleeve axis remains either parallel to, or at a predetermined angle relative to, the axis of the proximal part of the first arm).

The connecting portion may comprise an outer ring extending around the pivot axis. The connecting portion may incorporate an aperture within the outer ring aligned with the pivot axis between the first and second arms and arranged to allow an anatomical feature to be observed through the aperture along the pivot axis. In alternative embodiments, there may be no aperture encompassing or aligned with the pivot axis. The outer ring may form part of an adjustment mechanism for adjusting the angle between the first and second arms. The connecting portion may further comprise an inner ring defining the aperture, the inner ring being centred about the pivot axis and coupled to the outer ring by an arm extending from the outer ring.

The inner ring may define a tubular aperture, the tubular aperture being arranged to receive a guide pin such that the guide pin is aligned with the pivot axis. Alternatively, the outer ring (and the inner ring if one is provided) may be sized to receive the surgeon's finger so as to allow the anatomical reference point to be aligned with the goniometer pivot axis to be touched to ensure correct alignment. Alternatively, the goniometer may further comprise a rod having a central portion received within the inner ring, the central portion being arranged to slide through the inner ring and aligned with the pivot axis, and first and second enlarged end portions which cannot pass through the inner ring.

The outer ring may comprise a first ring portion and a second ring portion coupled together and rotatable with respect to one another about the pivot axis of the goniometer, the first arm being fixedly coupled to the first ring portion and the second arm being fixedly coupled to the second ring portion such that the angle between the first and second arms varies as the two ring portions rotate relative to one another.

The goniometer may further comprise a locking mechanism for locking the second arm to the first ring portion to fix the angle between the first and second arms. The locking mechanism may comprise a barrel disposed around either the first or second arms and rotatable between a first unlocked position and a second locked position in which the barrel bears against the outer ring preventing the first and second ring portions from rotating relative to one another. The locking mechanism may comprise a ratchet, the first ring portion further comprising a rack extending around the periphery of the connecting portion and the second arm further comprising a sprung pawl arranged to selectively engage the rack.

The outer ring may further comprise a gauge arranged to indicate the angle between the first and second arms.

According to a second aspect of the present invention there is provided a method of aligning a surgical instrument, the method comprising: setting an angle subtended at a pivot axis between first and second arms of a goniometer to a predetermined angle, the first and second arms being pivotally connected together about a pivot axis at a connecting portion, the goniometer further comprising an instrument connector coupled to the first arm; coupling the instrument connector to a surgical instrument; adjusting the position of the connecting portion until the pivot axis passes through an anatomical feature; and rotating the goniometer about the pivot axis until the second arm is aligned with an anatomical axis.

The instrument connector may comprise a sleeve arranged to pass over and slide along a surgical instrument, such that the surgical instrument can engage a bone, and the method may further comprise: positioning a tip of a drill guide at a required entry point upon a resected surface of a femoral neck; sliding the sleeve over the drill guide; and rotating the drill guide until the second arm of the goniometer is aligned with the femoral shaft and the pivot axis intersects the junction between the femoral neck and the femoral shaft. The axis of the bore of the sleeve may be arranged to be parallel to the axis of the first arm proximal to the connecting portion and intersects the pivot axis of the connecting portion, The connecting portion may incorporate an aperture aligned with the pivot axis between the first and second arms, and the method may further comprise observing an anatomical feature through the aperture.

The method may further comprise extending a guide pin through the aperture along the pivot axis until a tip of the guide pin touches the anatomical feature.

An advantage of embodiments of the present invention is that when the goniometer is used to align a surgical instrument or a prosthetic component coupled to the first arm, the aperture within the connecting portion of the goniometer allows the surgeon to observe the chosen anatomical feature, for instance an anatomical intersection, through the aperture to ensure that the goniometer is correctly positioned when the second arm is aligned with an anatomical axis. In order to reduce the risk of parallax errors, a reference pin may be inserted into the hole along the pivot axis to project the pivot axis onto the patient to ensure correct alignment. Alternatively, the hole may be sized so that the surgeon's finger can palpate the anatomical feature on the patient. Consequently, the risk of misaligning the instrument or prosthetic component is reduced.

BRIEF DESCRIPTION OF THE DRAWINGS

The present invention will now be described, by way of example only, with reference to the accompanying drawings, in which.

DETAILED DESCRIPTION OF THE INVENTION

Goniometers in accordance with embodiments of the present invention may be used during surgical procedures to align surgical instruments or prosthetic components with anatomical features and/or anatomical axes. In particular, goniometers in accordance with embodiments of the present invention may be used to aid the placement of a drill guide during a surgical procedure to prepare an end of a femur to receive a femoral prosthetic component.

A goniometer in accordance with certain embodiments of the invention comprises a first arm and a second arm pivotally coupled together at a connecting portion. The first arm is bent through approximately 90° towards its free end and terminates at a sleeve. The sleeve is arranged to be slidably disposed around a drilling guide. The axis of the sleeve is parallel to the axis of the first arm proximal to the pivotal connection to the second arm.

Figure 1:
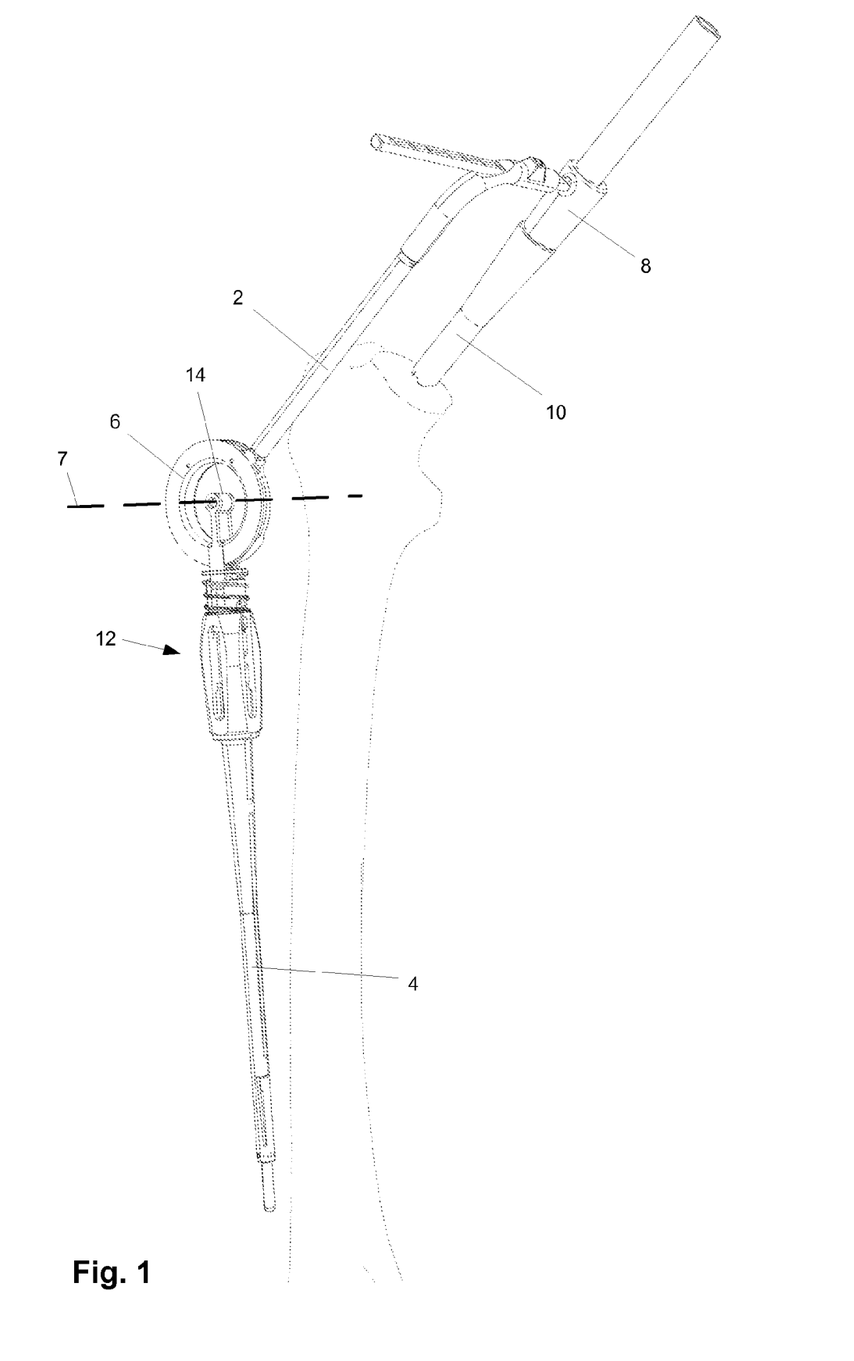
FIG. 1 schematically illustrates a goniometer in accordance with a first embodiment of the present invention in use during a surgical procedure to locate a drill guide at a required varus-valgus angle.

Referring first to FIG. 1, this schematically illustrates a goniometer in accordance with a first embodiment of the present invention in use during a surgical procedure to implant a femoral prosthetic component. The goniometer comprises a first arm 2 and a second arm 4 pivotally coupled to the first arm 2. The first and second arms are coupled together at a connecting portion 6. The second arm 4 is arranged to rotate relative to the first arm 2 about a pivot axis 7 (indicated by the dashed line) within the connecting portion 6. The first arm is bent through approximately 90° towards its free end and terminates at a sleeve 8. The sleeve 8 is arranged to be slidably disposed around a drilling guide 10. The sleeve 8 comprises a tubular component and has an axis which is parallel to the axis of the portion of the first arm 2 proximal to the connecting portion 6.

In certain embodiments of the present invention, and as illustrated in FIG. 1, the goniometer connecting portion 6 comprises an aperture which allows an anatomical feature to be directly viewed by a surgeon along the pivot axis 7. Furthermore, in certain embodiments and as illustrated in FIG. 1, the connecting portion 6 may comprise an inner ring 14 centred about the pivot axis 7 allowing the position of the anatomical reference point to be more closely defined relative to the pivot axis. The aperture or the inner ring 14 may be sized to allow the surgeon to palpate the reference point or to insert a pin extending along the pivot axis 7 until the pin touches the reference point. However, in alternative embodiments of the present invention there may be no such aperture and the anatomical reference point may not be directly visible to a surgeon inspecting the bone along the pivot axis 7. Furthermore, in alternative embodiments of the present invention, including for applications for the goniometer other than for aligning a drill guide during implantation of a femoral prosthesis, one or more other apertures may be provided as well or instead of an aperture at the pivot axis to allow anatomical features to be observed, palpated or touched with a pin. For instance, apertures may be provided at intermediate points along one or both arms.

For embodiments of the present invention without an aperture aligned with the goniometer pivot axis, it can be difficult to ensure that the pivot point of the goniometer is correctly located over the anatomical intersection. For instance, when a hip replacement procedure is performed following a posterior-lateral approach, the surgeon's viewpoint from the side of the theatre table can mean that it is difficult to ensure that the pivot point is positioned over the intersection. If the pivot is not correctly located, then pointing the end of the second arm towards the back of the patient's knee risks incorrectly locating the drilling guide. Consequently, the femoral implant axis may be misaligned.

The connecting portion of the goniometer illustrated in FIG. 1 includes an inner ring 14 that defines an aperture aligned with (that is, encompassing) the pivot axis 7 between the first and second arms 2, 4. Consequently, the connection between the femoral neck axis and the femoral shaft axis can be viewed through the ring by the surgeon looking along the pivot axis 7. In addition to viewing the anatomical intersection point through the ring the surgeon may optionally touch the intersection point through the ring in order to assist in locating the goniometer. As the anatomical feature can be directly viewed through the ring, the risk of misaligning the connecting portion 6 with the anatomical feature is reduced.

Figure 2:
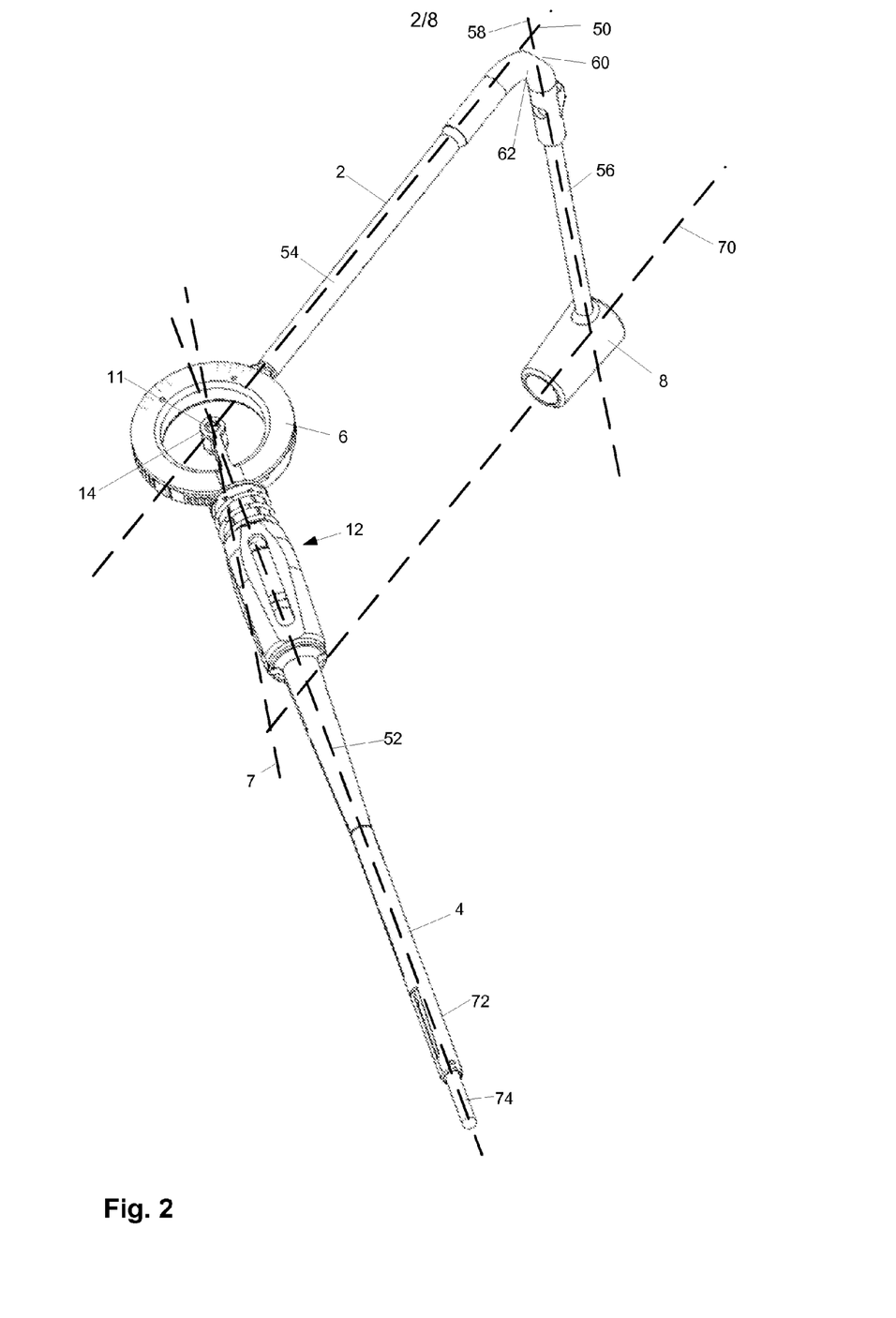
FIG. 2 is a perspective view of the goniometer of FIG. 1.

Referring now to FIG. 2 this is a schematic perspective illustration of the goniometer of FIG. 1, including the inner ring 14. Inner ring 14 is coupled to the second arm 4 as will be described in greater detail below in combination with FIGS. 3 to 5. Inner ring 14 also defines the aperture 11 which is aligned with the pivot axis 7 for the first and second arms 2, 4. The aperture 11 of inner ring 14 is sized to receive a guide pin (not illustrated), for instance a 3.2 mm diameter guide pin. A guide pin may thus slide through the inner ring 14 and be aligned with the pivot axis. The tip of the guide pin is positioned upon the anatomical reference feature in order to further assist in locating the connecting portion 6 of the goniometer. In an alternative embodiment of the present invention illustrated in FIG. 8 and described in greater detail below, a rod is permanently installed passing through the aperture 11 and arranged to slide through the aperture to come into contact with the anatomical reference point. The rod is prevented from sliding free from the ring by enlarged end portions. In yet another embodiment of the present invention, the aperture of the inner ring 14 may be sized to allow a tip of the surgeon's finger to pass through the connecting portion 6 to palpate the anatomical reference feature in order to provide finer control over positioning of the goniometer than for the goniometer of FIG. 1. The required anatomical reference feature may be marked upon the surface of the patient's bone prior to positioning the goniometer.

FIG. 2 illustrates the arrangement of the axes of the various parts of the goniometer. The first and second arms 2, 4 of the goniometer are coupled together via the connector portion 6 and can pivot relative to one another about pivot axis 7. The first arm 2, proximal to the connector portion 6, defines a longitudinal axis 50. The second arm 4 defines a longitudinal axis 52. Axes 50, 52 intersect at the pivot axis 7 and the pivot axis 7 extends normally to the plane defined by axes 50, 52.

Figure 3:
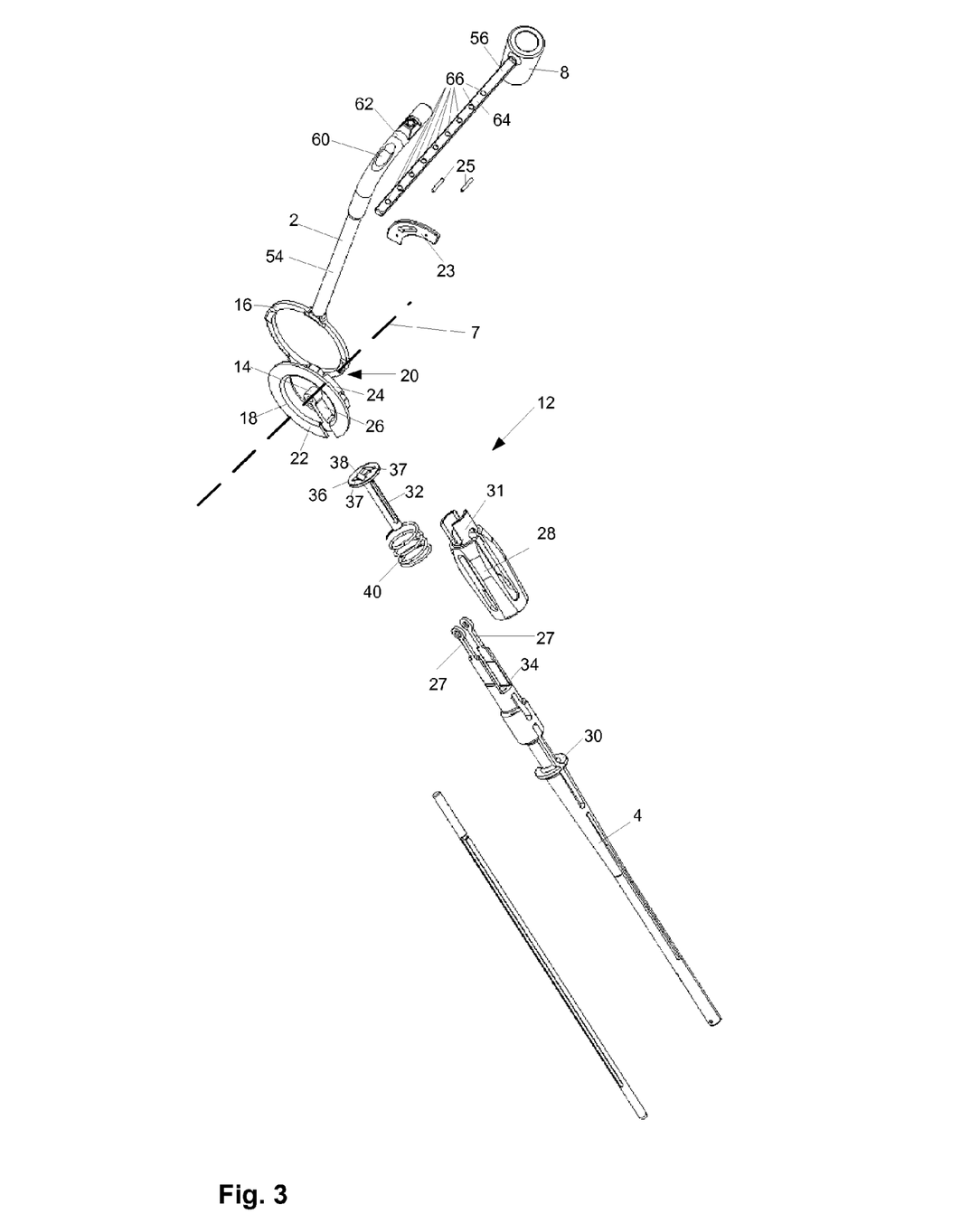
FIG. 3 is an exploded view of the goniometer of FIG. 1.

The first arm 2 comprises a first portion 54 extending along axis 50 and a second portion 56 which extends transversely from the first portion 52, for instance at 90°, and defines an axis 58 which is parallel to the pivot axis 4. The second portion 56 is arranged to slide relative to the first portion 54, passing through an orifice 60 within a curved portion 62 fixedly coupled to the first portion 54, as illustrated in the exploded view of FIG. 3. As illustrated in FIG. 3, the second portion 56 comprises a flattened side 64 and the orifice 60 comprises a corresponding flattened internal surface such that the second portion 56 of the first arm 2 cannot rotate within the orifice 60. The second portion may be prevented from rotating within the orifice 60 in other ways. For instance, the second portion 56 or the orifice 60 may comprise a pin and the other comprise an axial slot arranged to receive the pin such that the pin slides within the slot and prevents rotation. Alternatively, the second portion 56 may have any other form of non-circular cross section, for instance a generally T or D shaped cross section.

The second portion 56 further comprises a series of dimples 66 and the curved portion 62 comprises a spring loaded pin 68 arranged to engage a dimple 66 provide frictional resistance to sliding of the second portion 56 relative to the first portion 54. Other techniques for locking the second portion 56 to the first portion 54 will be readily apparent to the appropriately skilled person. For instance an integral leaf spring may be provided to bear against the second portion and to engage the dimples 66. Consequently the degree to which the second portion 56 extends from the first portion 54, and therefore the offset of the sleeve 8 relative to axis 50 of the second arm 2 may be adjusted. Adjusting the offset of sleeve 8 allows the goniometer to be adjusted for different sizes of patient such that the connecting portion 6 is closely positioned to the anatomical reference point, without the connecting portion 6 or the second arm 4 touching the patient.

Sleeve 8 defines a further axis 70 which extends at 90° to the axis 58 of the second part 56 of the first arm 2. Axis 70 extends parallel to the axis 50 of the first part 54 of the first arm 2 (as noted above, the second part 56 cannot rotate relative to the first part 54). Axis 70 therefore intersects the pivot axis 7 such that in use the drill guide 10 is always positioned such that it intersects the pivot axis 7. For instance, the anatomical reference point may be the intersection between a femoral neck axis and the femoral shaft axis. If the second arm is also aligned with the femoral shaft axis, by the second arm being directed towards the centre point of the back of the patient's knee then the drill guide will be aligned at a predetermined varus-valgus angle. The required version angle for the drill guide can be set by rotating the drill guide while maintain the alignment of the goniometer second arm and pivot axis.

As illustrated in FIG. 2, the second arm 4 comprises a tubular first portion 72 and a second 74 which is slidably received within the first portion 72. The second arm 4 is extendable by drawing the second portion 74 outwards, allowing the second arm to be adjustable for use with patients with legs of varying length. Extending the second arm 4 such that the tip of the second arm comes close to the patient's knee allows the second axis to be aligned parallel to the axis of the patient's femoral shaft more accurately. In alternative embodiments of the invention an extendable second arm may comprise an outer tube arranged to slide over a solid rod which is coupled to the connecting portion. Alternatively, the second arm may have one or more sections of different length arranged to be screwed or otherwise coupled together either to one another or directly to the connecting portion. Other forms of extendable arm will be readily apparent to the appropriately skilled person.

A surgical procedure for using the goniometer to determine the axis of a femoral implant will now be described. The implant may comprise a stem portion arranged to be implanted into a cavity extending generally along the femoral neck axis from a resection surface where the femoral head has been removed. The stem extends from the resection surface and comprises a locking taper arranged to receive a head prosthesis comprising a convex bearing surface. However, it will be appreciated that goniometers in accordance with the present invention may be used to align surgical instruments, and in particular drill guides, during implantation of alternative forms for prostheses. For instance, goniometers in accordance with the present invention may be used to align an initial bore extending into the end of a bone during implantation of resurfacing implants and monoblock implants (that is, where there is no locking taper and the bearing head is integrally formed with the femoral stem).

During pre-operative planning the required varus-valgus angle of the femoral component is determined. From an X-ray image of the hip in a medial-lateral plane the anatomical angle between the femoral shaft and the femoral neck is measured. This is used to set the goniometer to an appropriate varus-valgus angle, which may vary from the measured anatomical angle. Further X-ray images may be used to determine the maximum size of implant that can be accommodated and to determine the required position of the implant. An initial conservative resection is performed above the final osteotomy plane.

The pivotal connection between the first arm and the second arm of the goniometer incorporates a gauge and is lockable so that the corresponding angle required to set the required varus-valgus angle can be set between the first and second goniometer arms. The chosen implant angle is locked into position by rotating the locking barrel.

The end of the drill guide is placed against the resected surface with the tip of the drill guide in contact with the required drill insertion point. The goniometer sleeve is placed over the drilling guide and the sleeve is then allowed to slide along the drill guide while the goniometer is positioned. The drill guide can also pivot about its tip while the goniometer is positioned such that the direction of the axis of the drill guide relative to the bone varies. The second arm of the goniometer is aligned with the long axis of the femur by pointing the end of the second arm towards the back of the patient's knee. In alternative embodiments of the invention, rather than simply pointing the second arm at the back of the patient's knee in order to align the arm with the femoral shaft, the second arm may be modified so that the arm couples to the patient's leg. For instance, the arm may be arranged to couple to the distal femur may coupling to an intermedullarly fixator or an extramedullary fixator. The second arm may be arranged to couple to any other anatomical feature to facilitate alignment of the arm.

The pivot axis between the first and second goniometer arms is positioned over the required anatomical position (the connection between the femoral neck axis and the femoral shaft axis, specifically the intertrochanteric crest). Version alignment is achieved by rotating the drill guide until it is in line with the natural version of the femoral neck. When the pivot and the second arm are correctly positioned, the drilling guide is located at the correct varus-valgus angle and can be used to drill a hole into the femoral neck which defines the position for all following surgical steps and the implanted prosthesis. As discussed above, the pivot axis of the goniometer may be positioned by visual inspection (through the aperture, if available) or by passing a finger or guide pin through the aperture to touch the required anatomical position.

Referring to FIG. 3, this illustrates an exploded view of the connecting portion 6 of the goniometer of FIG. 2. FIG. 3 shows that the ring forming the connecting portion 6 is formed from first and second ring portions 16, 18 which are sandwiched together. A first ring portion 16 comprises a single ring which defines the outer perimeter of the connecting portion 6. Ring portion 16 is fixedly coupled to the first arm 2. Ring portion 16 further defines a series of notches 20 (not clearly visible in FIG. 3, but visible in the assembled view of the connecting portion 6 in FIG. 4) extending around its periphery which form part of the locking means 12 for locking the second arm 4 to the connecting portion 6 and thereby preserving the selected angle between the first and second arms 2, 4 (as will be explained in greater detail below).

The second ring portion 18 comprises a first flange part 22 which overlies the first ring portion 16 and a second ring part 24 which is seated within the first ring portion 16. The first and second ring portions 16, 18 are coupled together by plate 23 which sandwiches the first ring portion 16 against the flange part 22 of the second ring portion and connecting pins 25 which engage the second part 24 of the second ring portion 18. Ring portions 16, 18 are coupled together so that they cannot be separated from one another while allowing the ring portions 16, 18 to rotate relative to one another about the pivot axis 7. The second part 24 of the second ring portion 18 further comprises an arm 26 which extends to the inner ring 14 so that the ring 14 is fixed in position relative to the second ring portion 18 and aligned with the pivot axis between the first and second arms 2,4.

Second ring portion 18 is fixedly connected to the second arm 4 by forked end 27 which extends from the second arm and matches the shape of arm 26 and the inner ring 14. During manufacturing, once ring portions 16, 18 are brought together the forked end 27 of the second arm 4 is fitted over arm 26 and the forked end 27 is welded in place to the inner ring 14. As the first and second ring portions 16, 18 rotate relative to one another, the angle subtended between the first and second arms 2, 4 at the pivot axis 7 passing through inner ring 14 varies.

Locking means 12 comprises a barrel 28 rotatably disposed about the second arm 4. A first end of barrel 28 abuts an annular flange 30 extending from the second arm 4 so that it is prevented from sliding along second arm 4 away from the connecting portion 6. A second end of the barrel 28 comprises a narrowed tubular portion 31. Tubular portion 31 incorporates slits extending parallel to the second arm 4.

Locking means 12 further comprises a locking pin 32 slidably disposed within a cannula 34 within the second arm 4. Locking pin 32 is coupled to a flange 36 which extends from the side of second arm 4, the flange 36 in turn being coupled to a tooth 38 arranged to engage one of the notches 20 formed in the edge of first ring portion 16. The flange 36 incorporates twin slits 37 through which the forked end 27 of the second arm 4 extends to prevent locking pin 32 rotating relative to the second arm 4. A spring 40 is positioned around second arm 4 overlapping the tubular portion 31 of the barrel 28. Spring 40 is coupled between the thicker central portion of barrel 28 and flange 36. Spring 40 biases barrel 28 and flange 36 apart. As barrel 28 is prevented from sliding along second arm 4 by the flange 30, flange 36 and hence tooth 38 bears against and engages a notch 20.

As ring portion 16 rotates relative to ring portion 18, the tooth 38 travels along the series of notches 20 causing flange 36 to travel back and forth within cannula 34 by the same distance as the depth of a notch 20 thereby compressing spring 40. By holding the first arm 2 firm and moving second arm 4 around the connecting portion 6, tooth 38 sequentially engages teeth 20 under the action of spring 40 such that the angle between the first and second arms 2, 4 is encouraged to settle at one of a predetermined number of angular positions. The teeth 20 are spaced apart around the periphery of the connecting portion 6 at 5° intervals. In alternative embodiments the angular increments of the teeth may vary.

Barrel 28 is coupled to the second arm 4 via a screw thread within the barrel (not visible). The screw thread may be a two start M14 thread. It will be appreciated that the thread size and the pitch may vary, and also the screw thread may have one or more start points. Rotating the barrel 28 through half a turn about the second arm 4 causes the barrel 28 to slide towards the connecting portion 6. This causes the end of the tubular portion 31 of the barrel to move closer to, or into contact with, flange 36 preventing flange 36 from moving away from the connecting portion 6. As the locking pin 32 is not free to move away from the connecting portion 6, this locks the tooth 38 within a notch 20 so that the angle between the first and second arms 2,4 is fixed and further rotation of the ring portions 16,18 relative to one another is prevented. Thus, the angle subtended at pivot axis 7 between the first and second arms 2, 4 can be indexed in discrete steps equal to the spacing of notches 20, for instance 5° steps.

Figure 4:
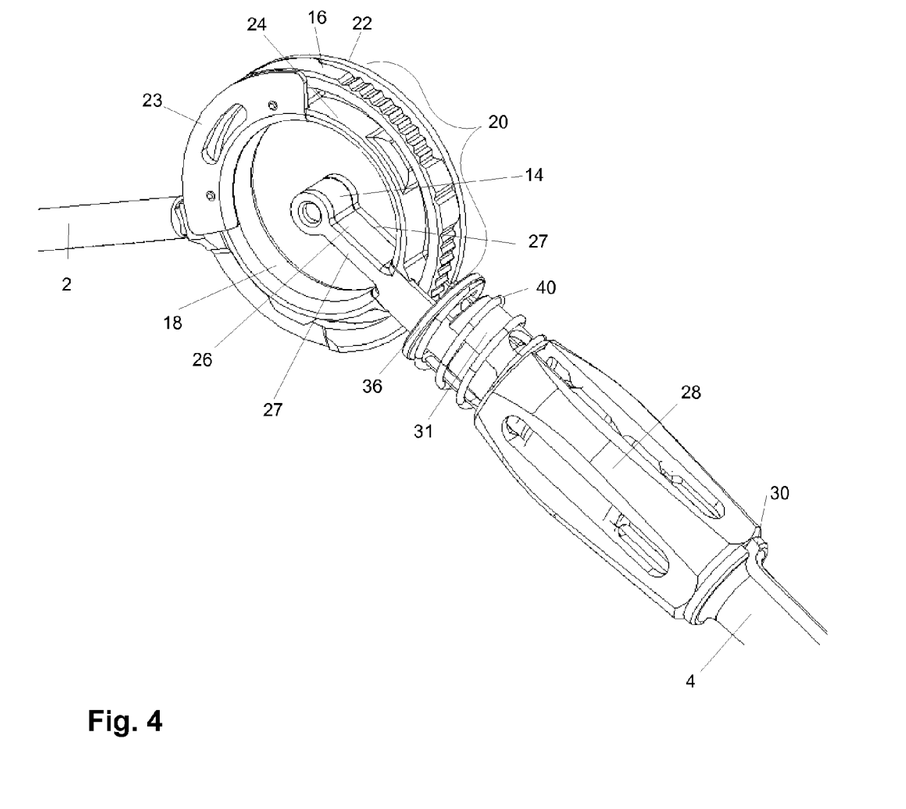
FIG. 4 is an enlarged view of the connecting portion of the goniometer of FIG. 1.
Figure 5:
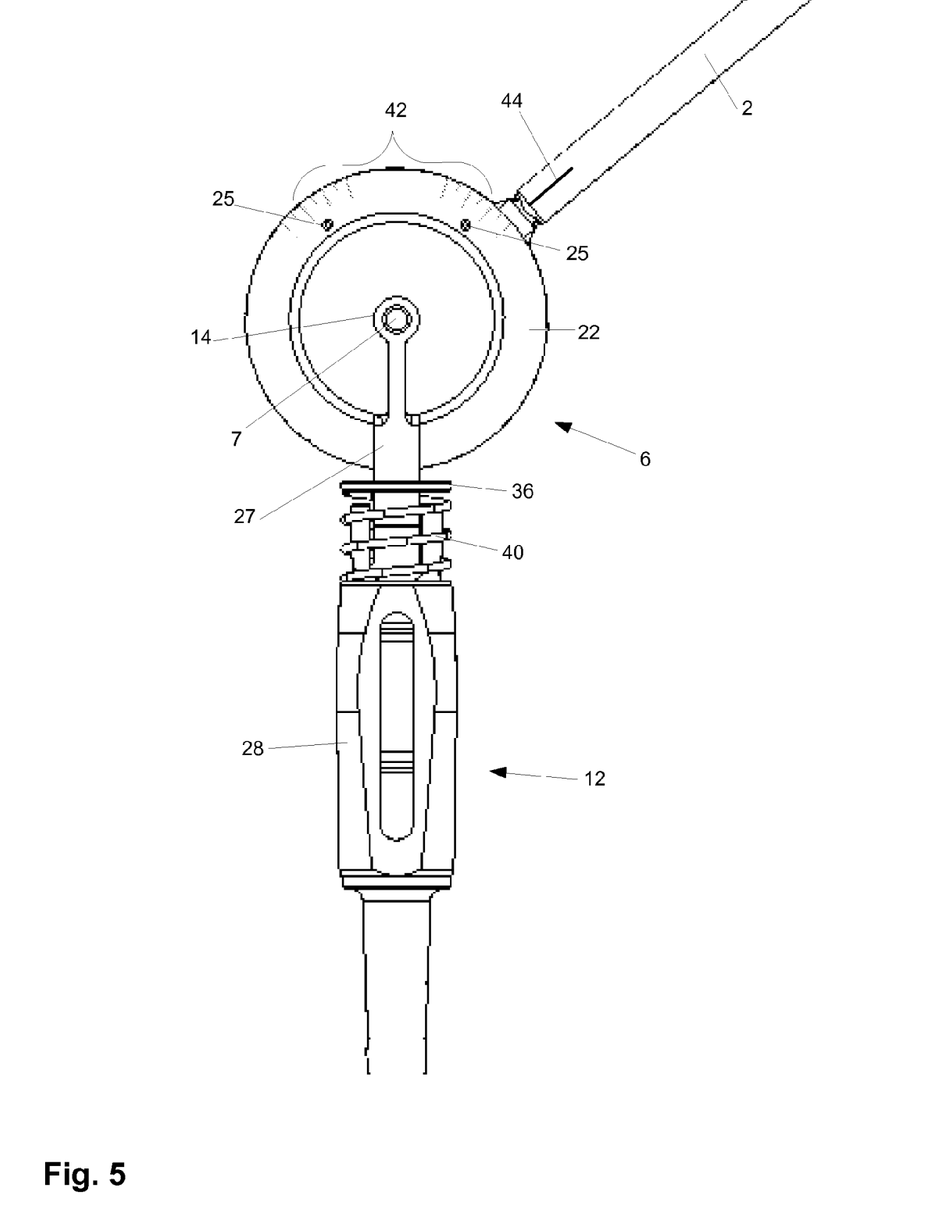
FIG. 5 is a plan view of the connecting portion of the goniometer of FIG. 1.

Referring now to FIG. 5, this illustrates a plan view of the connecting portion 6 showing the reverse side of the connecting portion 6 relative to the view of FIG. 4 (that is, with flange portion 22 uppermost). FIG. 5 shows a series of laser marks comprising a gauge 42 extending around part of the first ring portion 16. Gauge 42 indicates the angle between the first and second arms 2, 4 in 15° intervals. As the arms 2, 4 are rotated relative to one another, the point at which the first arm 2 is coupled to the connecting portion 6 shifts relative to the flange portion 22. The angle between the arms 2, 4 can be read by aligning a laser mark 44 on first arm 2 with the gauge 42. The angle between the arms 2,4 can be set by rotating the first arm 2 about the connecting portion to the required angle (in increments of 5° set by the spacing of the notches 20) and then turning barrel 28 through a half turn to fix locking pin 32 against the first ring portion 16. It will be appreciated that in alternative embodiments of the invention the spacing of the notches 20, and hence the size of each indexing step, and the frequency of the laser marks may vary. It will further be appreciated that in alternative embodiments of the invention the locking means 12 may be coupled to the first arm and the ring portions 16, 18 may be switched accordingly.

Figure 6:
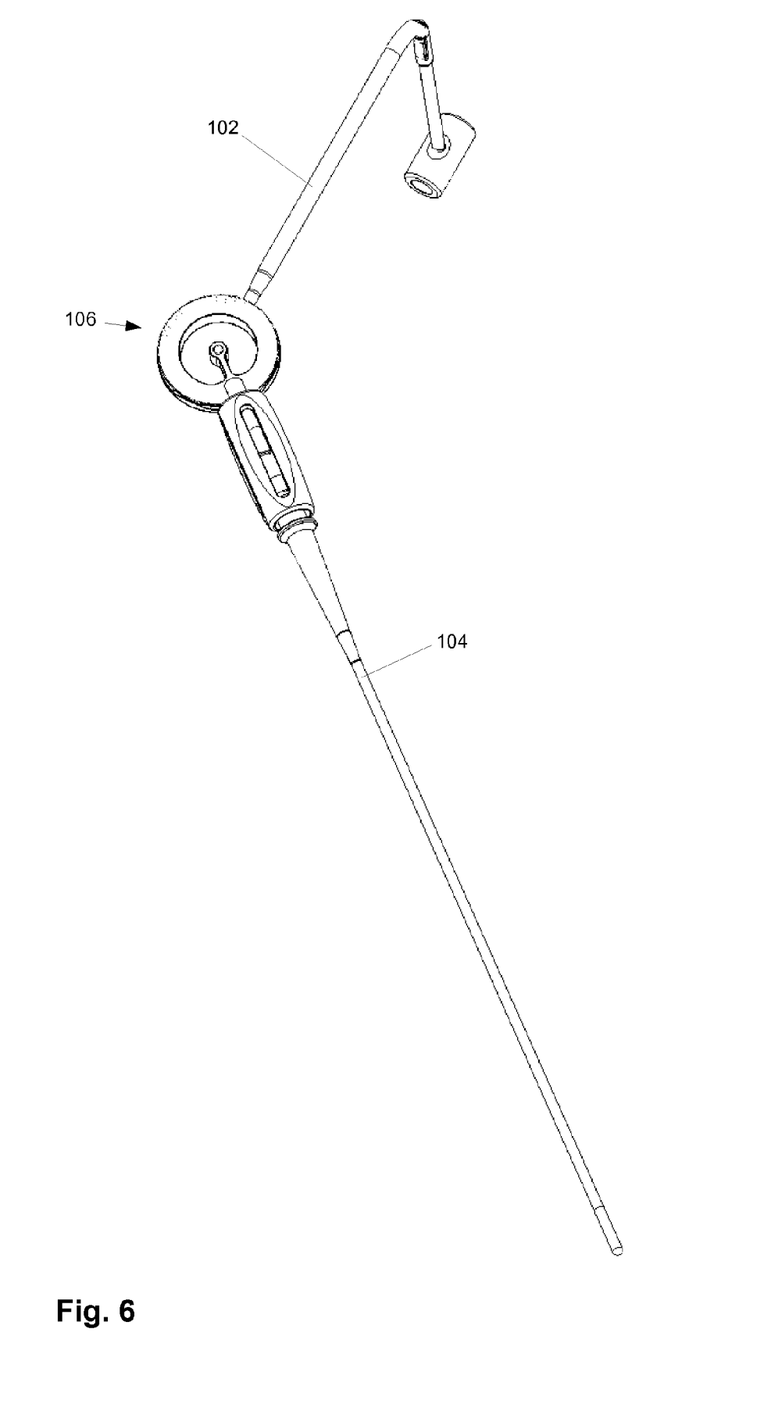
FIG. 6 is a perspective view of a goniometer in accordance with a second embodiment of the present invention.
Figure 7:
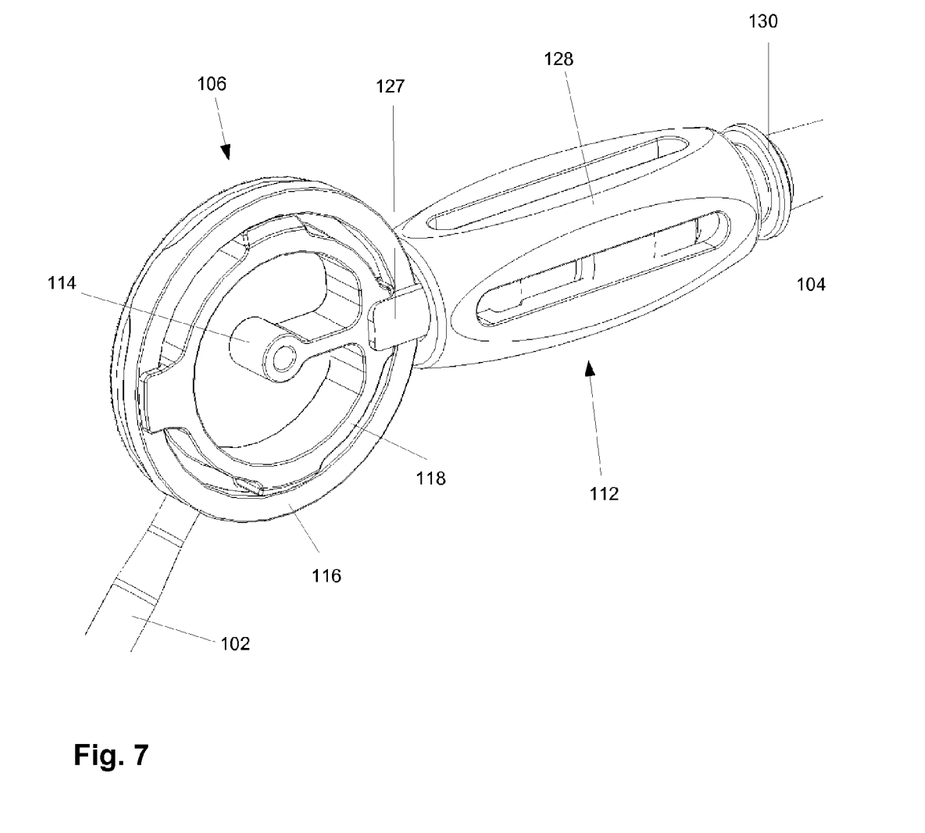
FIG. 7 is an enlarged view of the connecting portion of the goniometer of FIG. 6.

Referring now to FIGS. 6 and 7, these illustrate a goniometer in accordance with a second embodiment of the present invention in a perspective view and an enlarged reverse view of the connecting portion 6. The goniometer of FIGS. 6 and 7 is generally similar to the goniometer of FIGS. 1 to 5, and so references numbers increased by 100 are used to indicate corresponding features. Indeed the second embodiment of the invention generally comprises a simplified goniometer relative to the first embodiment, in which certain features are omitted, as will now be described.

The goniometer of FIGS. 6 and 7 comprises first and second arms 102, 104 coupled together at a connecting portion 106. Unlike the first embodiment, the second arm 104 is not telescopic and instead comprises an elongate arm arranged such that it is sufficiently short not to reach the knee of the smallest expected patient. The first arm 102 is generally the same as the first arm 2 for the first embodiment of the invention, described above.

The connecting portion 106 is generally similar and comprises a first ring 116 coupled to the first arm 102 and a second ring 118 coupled to the second arm 104 via a forked end 127 of the second arm 104 welded to the second ring. An inner ring 114 is again provided. However, unlike the goniometer of the first embodiment of the invention, the first ring 116 is not provided with notches, and rotation between the first and second arms 102, 104 is not indexed in discrete steps, rather they are free to rotate continuously. Locking mechanism 112 is simplified in that it comprises only an enlarged barrel 128 which can rotate about arm 104 between a first unlocked position in which it rests against flange 130 and a second locked position in which an end of the flange bears against the first and second rings 116, 118 preventing further rotation. As a further alternative, an additional bearing component may be provided between the enlarged barrel 128 and the first and second rings 116, 118 (or the additional bearing component may form part of the barrel 128) arranged to increase the locking surface area so as to reduce the possibility of the rings slipping relative to one another and the angle of the goniometer changing. Such an additional bearing component may be generally similar to a shoe for a drum brake.

Figure 8:
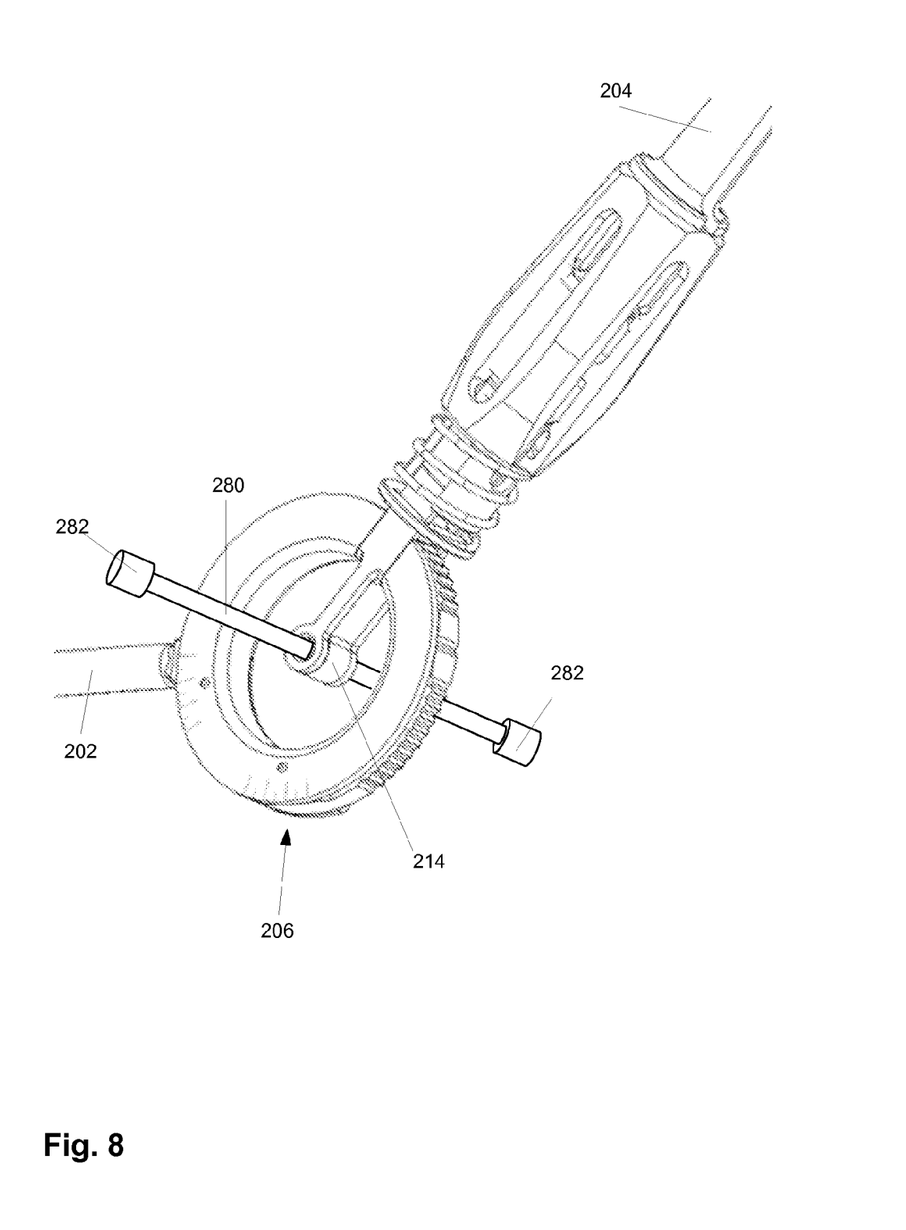
FIG. 8 is a perspective view of a goniometer in accordance with a third embodiment of the present invention.

Referring finally to FIG. 8, this illustrates a goniometer in accordance with a third embodiment of the present invention. The third embodiment is generally the same as the first embodiment and so reference numbers increased by 200 are used to refer to corresponding features. The goniometer of FIG. 8 differs in that a captured rod 280 passes through the inner ring 214 and is arranged to contact the anatomical reference point. Rod 280 is prevented from sliding from ring 214 by enlarged end portions 282 which cannot pass through ring 214. The length of rod 280 is chosen such that the rod 280 is long enough to accommodate typical variations in patient bone morphology.

It will be appreciated that although embodiments of the goniometer described above relate primarily to setting a varus-valgus angle for a surgical instrument during a hip replacement procedure, the present invention is not limited to this. Indeed, more generally goniometers in accordance with embodiments of the present invention may be used to accurately position surgical instruments or implants at a predetermined angle relative to an anatomical axis or feature about an axis extending through an anatomical feature, for instance an intersection of the patients bony anatomy. Alternatively, embodiments of the present invention may be used to measure angles taken from a patient by aligning the two arms with anatomical axes while the connecting portion is located over an anatomical feature. Whether goniometers according to the present invention are used to set an angle or measure an angle, the ability to observe an anatomical feature, while looking along the pivot axis, significantly aids the correcting positioning of the goniometer.

In alternative embodiments of the present invention the sleeve may be replaced with alternative coupling means for coupling the goniometer to other surgical instruments or prosthetic components and aligning those instruments or components with the axis of the first arm proximal to the connecting portion. Alternatively, the first arm and the sleeve or coupling means may be arranged to position the instrument or prosthetic component and a predetermined angle relative to the portion of the first arm proximal to the connecting portion.

In alternative embodiments of the present invention the locking means may form part of the first arm for adjusting the angle between the first and second arms.

Further modifications to, and applications of, the present invention will be readily apparent to the appropriately skilled person from the teaching herein, without departing from the scope of the appended claims.

The invention claimed is:
1. A goniometer comprising:
  a first arm having a first part extending along one longitudinal axis and a second part extending along a different longitudinal axis;
  a second arm;
  a connecting portion pivotally connecting the first arm to the second arm about a pivot axis that is parallel to the longitudinal axis of the second part of the first arm, wherein the connecting portion comprises:
    (a) an outer ring extending around the pivot axis; and

(b) an inner ring defining an aperture, the inner ring being (i) disposed within the outer ring, (ii) centered about the pivot axis and (iii) coupled to the outer ring by a third arm that extends from the outer ring, the aperture being aligned with the pivot axis between the first and second arms and arranged to allow an anatomical feature to be observed through the aperture along the pivot axis; and a tubular sleeve coupled to the second part of the first arm, the tubular sleeve being configured for coupling to a surgical instrument, the tubular sleeve having a bore having a longitudinal bore axis that intersects the pivot axis and is parallel to the longitudinal axis of the first part of the first arm;

wherein the first part of the first arm is coupled to the second part of the first arm in a manner that allows for relative translational movement between the first part and the second part so that the distance between the tubular sleeve and the longitudinal axis of the first part of the first arm is adjustable; and wherein the relative translational movement between the first part and second part of the first arm is in a direction transverse to the longitudinal axis of the first part of the first arm.

2. The goniometer of claim 1, further comprising a rod having a central portion received within the aperture and first and second enlarged end portions, the central portion being slidable through the aperture and aligned with the pivot axis, the first and second enlarged end portions being sized to prevent either the first or second enlarged end portions from passing through the aperture.

3. The goniometer of claim 1, wherein the second arm is extendable.

4. The goniometer of claim 1, wherein the inner ring defines a tubular aperture, and further comprising a rod having a central portion, the central portion received within the tubular aperture.

5. The goniometer of claim 4, wherein the outer ring comprises a first ring portion and a second ring portion coupled together and rotatable with respect to one another about the pivot axis, the first arm being fixedly coupled to the first ring portion and the second arm being fixedly coupled to the second ring portion such that the angle between the first arm and the second arm varies when the first ring portion and the second ring portion are rotated relative to one another.

6. The goniometer of claim 5, further comprising a locking mechanism for locking the second arm to the first ring portion to fix the angle between the first arm and the second arm.

7. The goniometer of claim 6, wherein the locking mechanism comprises a barrel disposed around either the first arm or the second arm such that the barrel is rotatable between a first unlocked position and a second locked position, wherein the barrel bears against the outer ring preventing the first ring portion and the second ring portion from rotating relative to one another.

8. The goniometer of claim 5, wherein the first ring portion further comprises a rack extending around at least a portion of the periphery of the connecting portion, and one of the first arm and the second arm further comprising a sprung pawl attached thereto to selectively engage the rack.

9. The goniometer of claim 1, wherein the outer ring further comprises a gauge arranged to indicate the angle between the first arm and the second arm.

10. The goniometer of claim 1, wherein the outer ring has a first side and a second side, and wherein the third arm comprises a first portion and a second portion, the first portion extends from the first side of the outer ring and the second portion extends from the second side of the outer ring.

11. The goniometer of claim 10, wherein the inner ring extends from the first portion to the second portion to define the aperture.

12. The goniometer of claim 1, wherein the third arm extends from the outer ring along an axis that is perpendicular to the pivot axis.

13. The goniometer of claim 1, wherein the outer ring has an outer perimeter and an inner perimeter, the inner perimeter defining an opening, and the inner ring is disposed within the opening.

* * * * *